US007262287B2

(12) United States Patent
Kang et al.

(10) Patent No.: US 7,262,287 B2
(45) Date of Patent: Aug. 28, 2007

(54) *HANSENULA POLYMORPHA* YAPSIN DEFICIENT MUTANT STRAIN AND PROCESS FOR THE PREPARATION OF RECOMBINANT PROTEINS USING THE SAME

(75) Inventors: Hyun-Ah Kang, Daejeon (KR); Sang-Ki Rhee, Daejeon (KR); Min-Jeong Sohn, Daejeon (KR); Jeong-Yoon Kim, Daejeon (KR)

(73) Assignees: Korea Research Institute of Bioscience and Biotechnology, Daejeon (KR); Leadbio, Inc., Daejeon (KR); Bioholdings Co., Ltd., Daejeon (KR)

( * ) Notice: Subject to any disclaimer, the term of this patent is extended or adjusted under 35 U.S.C. 154(b) by 105 days.

(21) Appl. No.: 10/518,377

(22) PCT Filed: Jun. 28, 2003

(86) PCT No.: PCT/KR03/01279

§ 371 (c)(1),
(2), (4) Date: Mar. 28, 2005

(87) PCT Pub. No.: WO2004/003204

PCT Pub. Date: Jan. 8, 2004

(65) Prior Publication Data

US 2005/0239074 A1    Oct. 27, 2005

(30) Foreign Application Priority Data

Jun. 29, 2002    (KR) .................... 10-2002-0037718

(51) Int. Cl.
*C12N 15/57* (2006.01)
*C12N 1/15* (2006.01)
*C12N 9/58* (2006.01)
*C12N 15/81* (2006.01)
*C12N 15/01* (2006.01)

(52) U.S. Cl. .................... 536/23.2; 435/69.1; 435/223; 435/255.6; 435/320.1; 435/455

(58) Field of Classification Search .................... None
See application file for complete search history.

(56) References Cited

U.S. PATENT DOCUMENTS 5,053,333 A * 10/1991 Yamamoto .................. 435/212

(Continued)

FOREIGN PATENT DOCUMENTS

KR    10-1999 0246932    12/1999

(Continued)

OTHER PUBLICATIONS

Bourbonnais et al., "Production of Full-Length Human Pre-elafin, an Elastase Specific Inhibitor, from Yeast Requires the Absence of a Functional Yapsin 1(Yap3p)," Protein Expression and Purification, vol. 20, p. 485-491 (2000).

(Continued)

*Primary Examiner*—Nashaat T. Nashed
*Assistant Examiner*—William W. Moore
(74) *Attorney, Agent, or Firm*—Greenblum & Bernstein, P.L.C.

(57) ABSTRACT

The present invention relates to a nucleic acid molecule comprising the HpYPS1 gene encoding *H. polymorpha* yapsin1, a polypeptide encoded by the nucleic acid molecule, a *H. polymorpha* mutant strain having reduced yapsin activity by mutation of the HpYPS gene encoding *H. polymorpha* yapsin1, a recombinant *H. polymorpha* strain expressing a foreign protein produced by introducing a gene encoding the foreign protein into the *H. polymorpha* mutant strain, and a process for preparing a foreign protein comprising culturing the recombinant *H. polymorpha* strain under conditions to express the foreign protein and isolating the foreign protein from the culture.

15 Claims, 10 Drawing Sheets

U.S. PATENT DOCUMENTS

| | | | |
|---|---|---|---|
| 5,506,120 A | * | 4/1996 | Yamamoto et al. ........ 435/69.7 |
| 5,612,198 A | * | 3/1997 | Brierley et al. ............ 435/69.9 |
| 5,726,038 A | * | 3/1998 | Christiansen et al. ...... 435/69.1 |
| 5,965,386 A | | 10/1999 | Kerry-Williams et al. |
| 6,110,703 A | | 8/2000 | Egel-Mitani et al. |
| 6,838,555 B2 | * | 1/2005 | Rhee et al. .............. 536/23.74 |

FOREIGN PATENT DOCUMENTS

| | | |
|---|---|---|
| KR | 10-2002 0017754 | 3/2002 |
| KR | 10-2002 0088841 | 11/2002 |
| WO | 98/01535 | 1/1998 |
| WO | 00/52133 | 9/2000 |
| WO | 03/057884 | 7/2003 |

OTHER PUBLICATIONS

Egel-Mitani et al., "Yield improvement of heterologous peptides expressed in *yps1*-disrupted *Saccharomyces cerevisiae* strains," Enzyme and Microbial Technology, vol. 26, pp. 671-677(2000).

Komano et al., "Purification and Characterization of the Yeast Glycosylphosphatidylinositol-anchored, Monobasic-specific Aspartyl Protease Yapsin 2 (Mkc7p)," The Journal of Biological Chemistry, vol. 274, No. 34, pp. 24431-24437 (1999).

Cawley et al., "Activation and Processing of Non-anchored Yapsin 1 (Yap3p)," The Journal of Biological Chemistry, vol. 273, No. 1, pp. 584-591 (1998).

Olsen et al., Biochem. J., 1999, vol. 339, pp. 407-411.

Kang et al., Appl. Microbiol. Biotechnol., 1998, vol. 50, pp. 187-192.

Gellissen, Appl. Microbiol. Biotechnol., 2000, vol. 54, pp. 741-750.

Copley et al., Biochem J. 1998, vol. 330, pp. 1333-1340.

Faber et al., Yeast, 1995, vol. 11, p. 1331-1344.

English Language Abstract of KOREAN 102002-0017754.

English Language Abstract of KOREAN 10-2002-0088841.

* cited by examiner

FIG. 1

```
   1  agttgagtcgcaatagtgtggcgaacttca  aatgcccttactgtccgcgaacaaccacca  ttgcccaggctgtgcaggccagatttgtta
  91  atttgtgaaaagtggaaaaaatttattccg  ctatgcctaaccgaagagcccgcaagaaga  ggcggacagaagacttttccagctcttcgg
 181  catctgaaaacgatagtgactccgagagcg  tgaccagtgtacaggaagagcagccggatg  cgcccgaaacatacacaatagatggcctgg
 271  acacgcaagaggtgtctgacagcacacagg  tgagactccaacagctgaacgcagacaggt  tggccagcatagagcaaagcctttcaggca
 361  acctcaaactggacataaacgcagtacgcc  agatagatgatgtgcgtgagcagctgcaga  acgagtatttgaagaaattgcttgtcacat
 451  attctgaggacctggatgcgctgcgtcaga  aaaccgatttcaaggaaaactcactcaaaa  ccctcgcccgtcttctcaaagagagcggaa
 541  acatatttgatgatggaactctcaagtcgc  tagttgagtgatgtatatgataatgtctaa  ttttaattttcatcagtgtgcaagatctgg
 631  gcttagccgttctaaatggtatattcaggc  tgtgcaagccacatttaaaattaccccatc  ggtttttaaattctattgttagaaattagg
 721  atctacatagaggtagagtgagcaacagaa  cattgtttgctatccgggccctccgactgg  aacgtcttaccttcagctactatttattca
 811  gaaaaaagagtgcattttcatctatcaagg  tctcaaagtgtcgaatcaaatcactagtat  ttttccgagactaaaaaaaagttgacaca 901  ATGAAAGTTGCTACACTGTTTTTCTTGGCT  TCGAGTGTCTGTGTGCTGGGAGACCCACAG  TTCGTGAAACTGGAGGCCTCTGTTCTTCGG
       M  K  V  A  T  L  F  F  L  A   S  S  V  C  V  L  G  D  P  Q    F  V  K  L  E  A  S  V  L  R
 991  GGATCCACTTACAAGGATTCCCAGAAGGGG  GCCAAGCCGTTCATGTTGGAAAAGAGGGCT  GATGACGGCTCGGTCACGATGGAATTGCAG
       G  S  T  Y  K  D  S  Q  K  G   A  K  P  F  M  L  E  K  R  A    D  D  G  S  V  T  M  E  L  Q
1081  AACGCCCAGTCTTTCTACCAAGTCGAGATC  GAGATAGGATCTGATAAGCAGAAGGTGGGG  GTTTTGATTGATACCGGTTCCTCGGACTTG
       N  A  Q  S  F  Y  Q  V  E  I   E  I  G  S  D  K  Q  K  V  G    V  L  I  D  T  G  S  S  D  L
1171  TGGGTGATGAACTCGAATAACTCTTACTGT  TCGTCTTCCAGCACTAAAAAATTGAAACGG  GACGGACCGGCCGATGCGCTACAAAAAGGA
       W  V  M  N  S  N  N  S  Y  C   S  S  S  S  T  K  K  L  K  R    D  G  P  A  D  A  L  Q  K  G
1260  CGCGATCTTTCCGACCTGTACAATTTCAAC  TCTCCAAACGAAGACAACAATGCAAAAGGA  TTCTTGGGTGGCTGGGGAGACTTGACCACA
       R  D  L  S  D  L  Y  N  F  N   S  P  N  E  D  N  N  A  K  G    F  L  G  G  W  G  D  L  T  T
1351  GTAGAGACTGCAACCCAGGATGAGACACAG  ACGGCTCTCGCTGCGCAGGCCACCGTGGAC  TGCTCGCTATACGGAACGTTCAATCCTTCA
       V  E  T  A  T  Q  D  E  T  Q   T  A  L  A  A  Q  A  T  V  D    C  S  L  Y  G  T  F  N  P  S
1441  ACGTCCAATTCGTTCCACAACAACGGCACC  ACATTTGAGATTTCGTACGCGGACCGCACT  TTTGCCCGTGGAACCTGGGGCTACGATGAT
       T  S  N  S  F  H  N  N  G  T   T  F  E  I  S  Y  A  D  R  T    F  A  R  G  T  W  G  Y  D  D
1531  GTCACTTTCAATGGTGTCACGGTTAACGAT  CTCTCGTTGGCCGTGGCAGATGAAACAGAT  TCTTCGACTGGTGTTTTTGGTATCGGATTG
       V  T  F  N  G  V  T  V  N  D   L  S  L  A  V  A  D  E  T  D    S  S  T  G  V  F  G  I  G  L
1621  AGGGAATTGGAAACCACATACTCAGGAGGC  GGACCACAGCATTACATCTACGACAACTTA  CCTTTCAAAATGGTCGACCAGGGACTCATC
       R  E  L  E  T  T  Y  S  G  G   G  P  Q  H  Y  I  Y  D  N  L    P  F  K  M  V  D  Q  G  L  I
1711  AATAGAGCCGCCTATTCCGTCTACCTGAAC  TCAACTGAGTCCAGCACTGCCTCGATCCTC  TTCGGTGCGGTTGACCAAAGCAAATATACC
       N  R  A  A  Y  S  V  Y  L  N   S  T  E  S  S  T  A  S  I  L    F  G  A  V  D  Q  S  K  Y  T
1801  GGAAGTCTTGGCTTGCTTCCTATCATCAAC  ACGGCTGCTTCCTACGGTTACCAAAAGCCT  CTAAGGCTCCAAATCACCCTGTCTGCCATT
       G  S  L  G  L  L  P  I  I  N   T  A  A  S  Y  G  Y  Q  K  P    L  R  L  Q  I  T  L  S  A  I
1891  ACGGTCAGCGACTCCAGAGGACAGCAAGCA  AGCATTGGTTCAGGAGCTGCTGCTGCACTT  CTTGATACCGGAACGACTTTGACGTATGCT
       T  V  S  D  S  R  G  Q  Q  A   S  I  G  S  G  A  A  A  A  L    L  D  T  G  T  T  L  T  Y  A
1981  CCAAGCGAGATTGTCGAGAAACTTGCTGAA  ACCCTAGGCTTCGACTACAGCAGCTCTGTC  GGGGCCTACGTGGCAAGATGCAGGGACGTT
       P  S  E  I  V  E  K  L  A  E   T  L  G  F  D  Y  S  S  S  V    G  A  Y  V  A  R  C  R  D  V
2071  GATAGCTACGCTGTCAACTTCGACTTCCAG  GGTAAAGTGATTGAAGCTCCTTTGAGTTCC  TTCCTGATTGCTCTGCAAACCAACTCCGGA
       D  S  Y  A  V  N  F  D  F  Q   G  K  V  I  E  A  P  L  S  S    F  L  I  A  L  Q  T  N  S  G
2161  GAAGTTTCCTCCTACTGCGCATTGGGTATT  TTCTCCTCTGGAGACGAATCCTTCACGCTC  GGCGATACTTTCCTGCGAAACGCCTACTTT
       E  V  S  S  Y  C  A  L  G  I   F  S  S  G  D  E  S  F  T  L    G  D  T  F  L  R  N  A  Y  F
2251  GTGGCTGACCTCGAGGGATATCAAATCGCT  ATAGCTAACGTGAACCTGAATCCTGGAGCC  GAGCAAATTGAGGTCATCTCAGGCAACTCC
       V  A  D  L  E  G  Y  Q  I  A   I  A  N  V  N  L  N  P  G  A    E  Q  I  E  V  I  S  G  N  S
2341  ATTCCTTCTGCTTCGTCGGTTTCCGATTAC  TCCAATACCTGGGGCGCCTCTGCCACCGCT  TTGGACACTGACAGGCCTACTACTCTGGGA
       I  P  S  A  S  S  V  S  D  Y   S  N  T  W  G  A  S  A  T  A    L  D  T  D  R  P  T  T  L  G
2431  TCTGTGACTGCTGTGGGCGATGAAAAGAGTG  ACCTCGACCAAGAAGGTTTCGAGTGTGAAG  ACAAGCACTTCGTCCGGGTCCGGGTCCACT
       S  V  T  A  V  G  D  E  R  V   T  S  T  K  K  V  S  S  V  K    T  S  T  S  S  G  S  G  S  T
2521  TCGGAGTCGTCTACGTCCAGTTCGCATTCC  AGCAATGGCCCAAGGACAGTAGGCTTTAGT  TTGTGTGCCGTTTTGTGCGCATTCTTGATT
       S  E  S  S  T  S  S  S  H  S   S  N  G  P  R  T  V  G  F  S    L  C  A  V  L  C  A  F  L  I
2611  TCTATACTAGTTGTTTGCtagatctgaagt  tctaaggggctttagtcttcatttatgatt  ttttttatttggaccgcctcgaattgttt
       S  I  L  V  V  C  -
2701  ttccgacgggtctactttaaagctgcaaga  tctcgtttagcgtcgtttatttctcgttcg  tttagtgacaaaaaaacagaaaaaaaaact
2791  ataaaaagcggtatataaccttatatttt   gataaacatgagcagcgaaattaagctagc  accaaaggattacgagaaggacaaggagtt
2881  cgccaaggctctgcatggcaaggacgccgc  gagcgctacaggaatgagtgcttgggtgaa  gaaggacaaggaagctcaaaaagtcgcgat
2971  ggaaggatatttcaagcactgggacgggaa  aaccgacgaggagactgaaaagtcgagact  cgaggactactcgacgctcaccaagcacta
3061  ctacaacctggtgacggatttctacgagta  tggatggggatcctcgttccactttttccag  atactacaaggggagagccatttagacaagc
3151  t
```

FIG. 2

```
HpYPS1 : MKVATLFFLASSV----CVLG-------------DPQFVKLEASVLRGSTYKDSQKGAKPFMLEKRADDG   :  53
ScYPS1 : MKLRTVRSAVLSSLFASQVLGKIIPAANKRDDDSNSKFVKLPFEKLYGDSLENVGSDKKPEVRLLKRADG    :  70
ScYPS2 : MKLSVLTFVVDALLVCSSIVDAGV--TDFPSLPSNEVYVKMNFQKKYGSSFENALDDTKGRTRLMTRDDD   :  68
ScYPS3 : MKLQLAAVATLAVL-TSPAFGRVLP---------DGKYVKIPFTKK----------KNGDNGELSKRSNG   :  50

HpYPS1 : SVTMELQNAQSFYQVELEIGSDKQKVGVLIDTGSSDLWVMNSNNSYCSSSTKKLKR---DGPADALQKG    : 120
ScYPS1 : YEEIIITNQQSFYSVDLEVGTPPQNVTVLVDTGSSDLWIMGSDNPYCSSNSMGSSRRRVIDKRDDSSSGG  : 140
ScYPS2 : YELVELTNQNSFYSVELDIGTPPQKVTVLVDTGSSDLWVTGSDNPYCSTKKKDTTGSSF--KQVNKDALA  : 136
ScYPS3 : HEKFVLANEQSFYSVELAIGTPSQNLTVLLDTGSADLWVPGKGNPYCGS--------------------   :  99

HpYPS1 : RDLSDLYNFNSPNEDNNAKGFLGGWGDLTTVETATQDETQTALAAQATVDCSLYGTFNPSTSNSFHNNGT  : 190
ScYPS1 : SLINDINPFGWLTGTGSAIGP-----TATGLGGGSGTATQSVPASEATMDCQQYGTFSTGGSTFRSNNT   : 205
ScYPS2 : SVVESV--F------TEISY-----DTTIVTSEATATFDSTASTSQLIDCATYGTFNTSKSSTFNSNNT   : 192
ScYPS3 : ------------------------------------VMDCDQYGVFDKTKSSTFKANKS            : 122

HpYPS1 : T-FEISYADRTFARGTWGYDDVTFNGVTVNDLSLAVADETDSSTGVFGIGLRELETTYSG----GPQHY   : 255
ScYPS1 : Y-FSISYGDGTFASGTFGTDVLDLSDLNVTGLSFAVANETNSTMGVLGIGLPELEVTYSGSTASHSGKAY  : 274
ScYPS2 : E-FSIAYGDTTFASGTWGEDQLSLNDLNITGLSFAVANESNSTVGVLGIGLPGLESTYSGVSLSSVQKSY  : 261
ScYPS3 : SPFYAAYGDGTYAEGAFGQDKLKYNELDLSGLSFAVANESNSTFGVLGIGLSTLEVTYSGKVAIMDKRSY  : 192

HpYPS1 : IYDNLPFKMVDQGLINRAAYSVYLNSTESSTASILFGAVDQSKYTGSLGLLPLINTAASYGYQKPLRLQI  : 325
ScYPS1 : KYDNFPIVLKNSGAIKSNTYSLYLNDSDAMHGTILFGAVDHSKYTGTLYTIPIVNTLSASGESSPIQFDV  : 344
ScYPS2 : TYNNFPMVLKNSGVIKSTAYSLFANDSDSKHGTILFGAVDEGKYAGDLYTIPIINTLQHRGYKDPIQFQV  : 331
ScYPS3 : EYDNFPLFLKHSGAIDATAYSLFLNDESQSSGSILFGAVDHSKYEGQLYTIPLVNLYKSQGYQHFVAFDV  : 262

HpYPS1 : TLSAITVSDSRGQQ--ASIGSGAAAALLDTGTTLTYAPSEIVEKLAETLGFDYSSVGAVVARGRDV--D   : 391
ScYPS1 : TINGIGISDSGSSNK--TLTTTKIPALSDSGTTLTYLPQTVVSMIATELGAQYSSRIGYYVLDCPSD--D  : 410
ScYPS2 : TLQGLGTSKGDKEDNLTTLTTTKIPVLLDSGTTISYMPTELVKMLADQVGATYSSAYGYYIMDQIKEMEE  : 401
ScYPS3 : TLQGLGL---QTDKRNITLTTTKLPALLDSGTTLTYLPSQAVALLAKSLNASYSKTLGYLEYTCPSS-DN  : 328

HpYPS1 : SYAVNFDFQGKVIEAPLSSFLIALQTNSGEVSSYCALGIFS-SGDESFTLGDTFLRNAYFVADLEGYQIA  : 460
ScYPS1 : SMEIVFDFGGFHINAPLSSFIISTGT---T----CLLGIIPTSDDTGTILGDSFLTNAYVVYDLENLEIS  : 473
ScYPS2 : ESSIIFDFGGFYLSNWLSDEQLVTDSRSNI----CILGIAPQSDPT-IILGDNFLANTYVVYDIDNMEIS  : 466
ScYPS3 : KTSVAFDFGGFRINAPLSDFTMQTSV--GT----CVLAIIPQAGNATAILGDSFLRNAYVVYDLDNYEIS  : 392

HpYPS1 : IANVNLNPGAEQIEVISGNSIPSASSVSDYSNTWGASATALDTDRPTTLGSVTAVG-----DERVTSTKK  : 525
ScYPS1 : MAQARYNTTSENIEIITS-SVPSAVKAPGYTNTWSTSASIVTGGNIFTVNSSQTASF-----------   : 529
ScYPS2 : MAQANFSDDGEYIEIIES-AVPSALKAPGYSSTWSTYESIVSGGNMFSTAANSSISYFASTSHSATSSSS  : 535
ScYPS3 : LAQAKYGTGKENVEVIKS-TVPSAIRAPSYNNTWSNYASATSGGNIFTT-----VRTFNGTS-TATTTRS  : 455

HpYPS1 : VSSVKTSTSSGSGSTSESSTSSSHS---------SNGPRTVGFSLCAVLCAFLISILV------------  : 574
ScYPS1 : ---------SGNLTTSTASATSTSS------------KRNVGDHIVPSLPLTLISLLFA----------   : 567
ScYPS2 : SKGQKTQTSTAALSISKSTSSTSSTGMLSPTSSSSPRKENGGHNLNPPFFARFITAIFH----------   : 594
ScYPS3 : TTTKKTNSTT----TAKSTHKSKRALQRAATNSASSIRSTLGLLLVPSLL--ILSVFFSPRHSAGSIISN  : 519

HpYPS1 : -VC-  : 576
ScYPS1 : --FI  : 569
ScYPS2 : --HI  : 596
ScYPS3 : PVYG  : 523
```

Lane M: Molecular marker
1: wild type, o-h reaction
2: wild type, 2-h reaction
3: wild type, 4-h reaction
4: wild type, 6-h reaction
5: wild type, 24-h reaction
6: distilled water + hPTH, o-h reaction
7: mutant strain, o-h reaction
8: mutant strain, 2-h reaction
9: mutant strain, 4-h reaction
10: mutant strain, 6-h reaction
11: mutant strain, 24-h reaction
12: hPTH 100 ng
13: hPTH 200 ng

FIG. 7
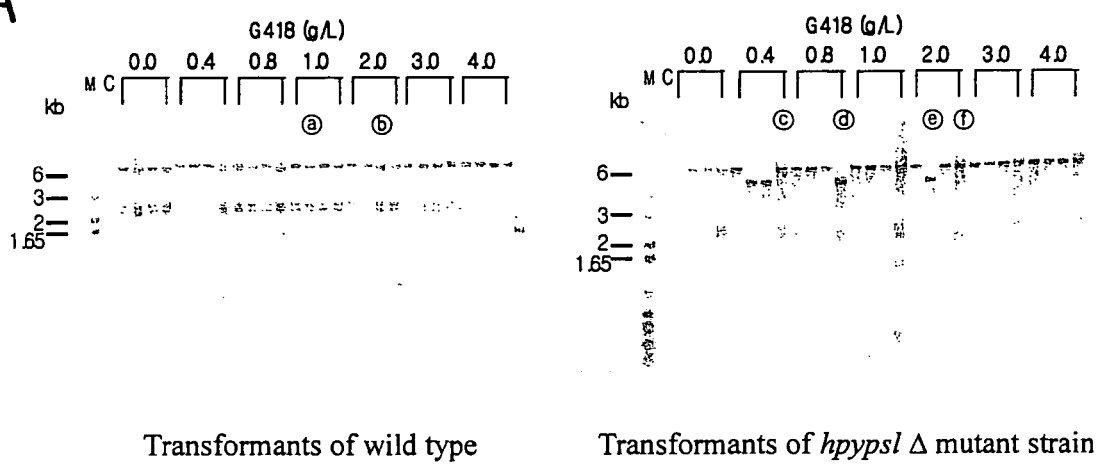
Transformants of wild type        Transformants of *hpypsl* Δ mutant strain
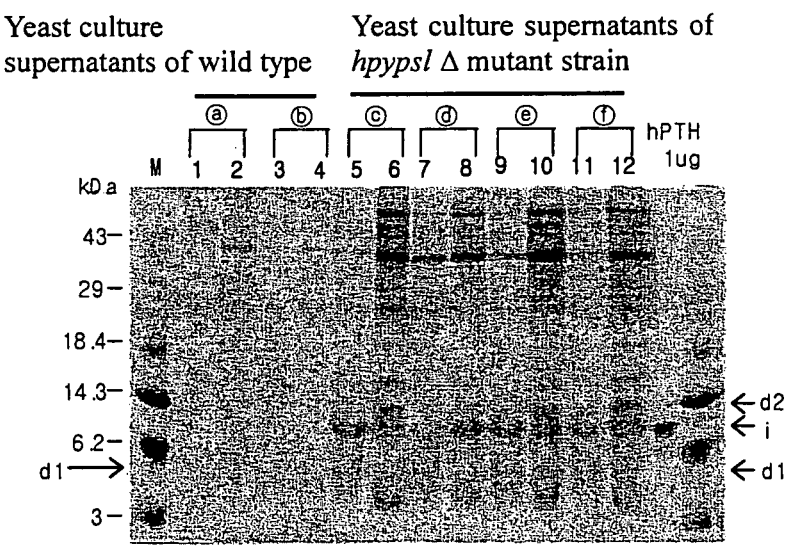
Lane 1, 3, 5, 7, 9, 11 : 12hr after initiation of the cultivation
Lane 2, 4, 6, 8, 10, 12 : 24hr after initiation of the cultivation

FIG. 8
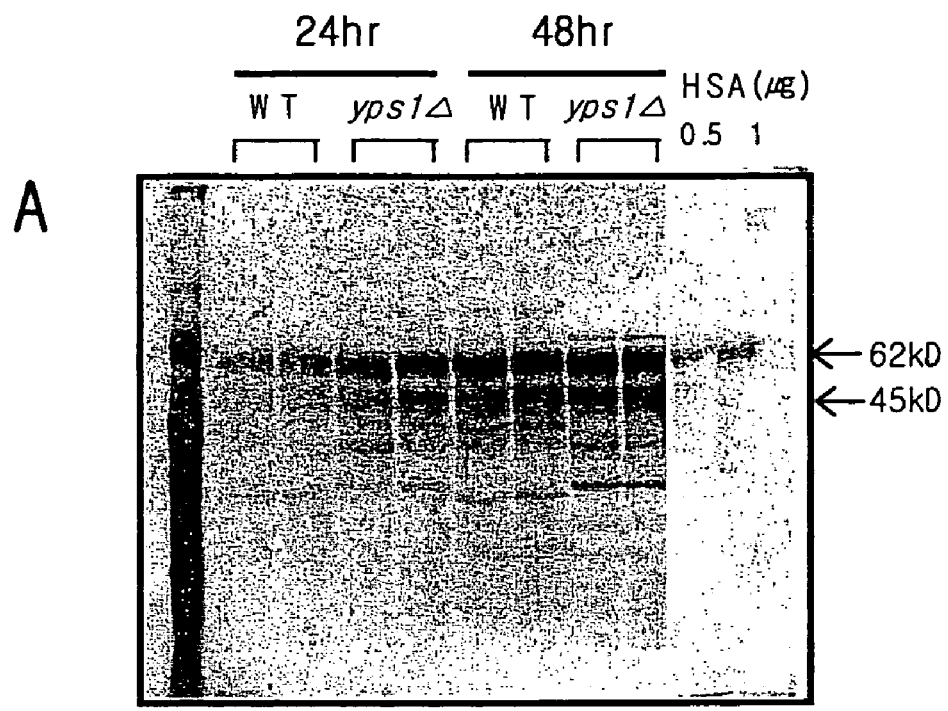
A
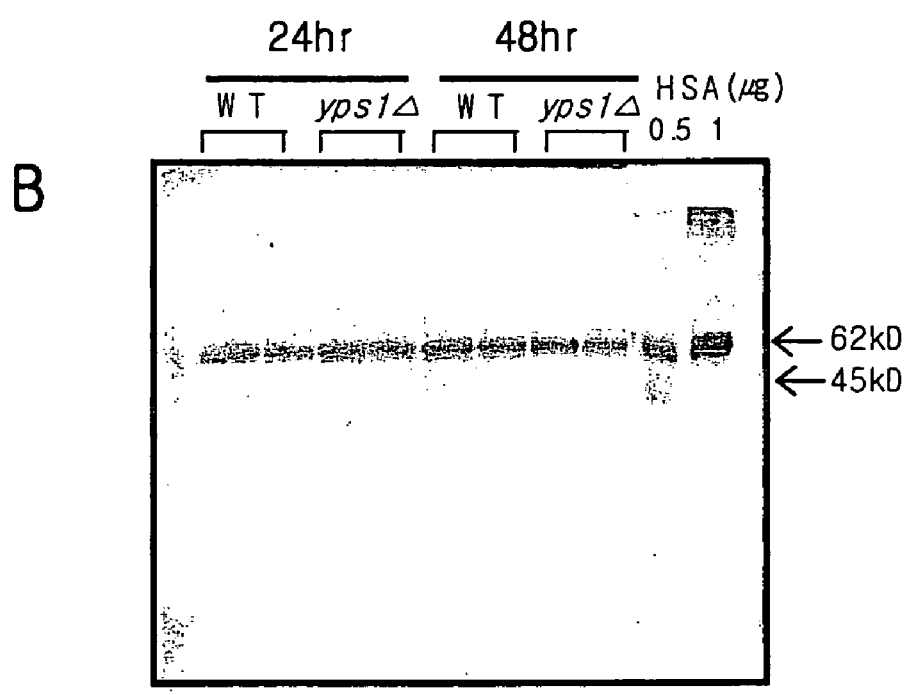
B

SEQUENCE LISTING

<160> NUMBER OF SEQ ID NOS: 16

<210> SEQ ID NO 1
<211> LENGTH: 3151
<212> TYPE: DNA
<213> ORGANISM: Hansenula polymorpha

<400> SEQUENCE: 1

```
agttgagtcg caatagtgtg gcgaacttca aatgccctta ctgtccgcga acaaccacca      60
ttgcccaggc tgtgcaggcc agatttgtta atttgtgaaa agtggaaaaa atttattccg     120
ctatgcctaa ccgaagagcc cgcaagaaga ggcggacaga agactttcc agctcttcgg     180 catctgaaaa cgatagtgac tccgagagcg tgaccagtgt acaggaagag cagccggatg     240
cgcccgaaac atacacaata gatggcctgg acacgcaaga ggtgtctgac agcacacagg     300
tgagactcca acagctgaac gcagacaggt tggccagcat agagcaaagc ctttcaggca     360
acctcaaact ggacataaac gcagtacgcc agatagatga tgtgcgtgag cagctgcaga     420
acgagtattt gaagaaattg cttgtcacat attctgagga cctggatgcg ctgcgtcaga     480
aaaccgattt caaggaaaac tcactcaaaa ccctcgcccg tcttctcaaa gagagcggaa     540
acatatttga tgatggaact ctcaagtcgc tagttgagtg atgtatatga taatgtctaa     600
ttttaatttt catcagtgtg caagatctgg gcttagccgt tctaaatggt atattcaggc     660
```

```
tgtgcaagcc acatttaaaa ttaccccatc ggttttaaa ttctattgtt agaaattagg    720
atctacatag aggtagagtg agcaacagaa cattgtttgc tatccgggcc ctccgactgg    780
aacgtcttac cttcagctac tatttattca gaaaaagag tgcattttca tctatcaagg    840
tctcaaagtg tcgaatcaaa tcactagtat tttttccgag actaaaaaaa agttgacaca    900
atgaaagttg ctacactgtt tttcttggct tcgagtgtct gtgtgctggg agacccacag    960
ttcgtgaaac tggaggcctc tgttcttcgg ggatccactt acaaggattc ccagaagggg   1020
gccaagccgt tcatgttgga aaagagggct gatgacggct cggtcacgat ggaattgcag   1080
aacgcccagt ctttctacca agtcgagatc gagataggat ctgataagca aaggtgggg    1140
gttttgattg ataccggttc ctcggacttg tgggtgatga actcgaataa ctcttactgt   1200
tcgtcttcca gcactaaaaa attgaaacgg gacggaccgg ccgatgcgct acaaaaagga   1260
cgcgatcttt ccgacctgta caatttcaac tctccaaacg aagacaacaa tgcaaaagga   1320
ttcttgggtg gctggggaga cttgaccaca gtagagactg caacccagga tgagacacag   1380
acggctctcg ctgcgcaggc caccgtggac tgctcgctat acggaacgtt caatccttca   1440
acgtccaatt cgttccacaa caacggcacc acatttgaga tttcgtacgc ggaccgcact   1500
tttgcccgtg aacctggggg ctacgatgat gtcactttca atggtgtcac ggttaacgat   1560
ctctcgttgg ccgtggcaga tgaaacagat tcttcgactg gtgtttttgg tatcggattg   1620
agggaattgg aaaccacata tcaggaggc ggaccacagc attacatcta cgacaactta   1680
cctttcaaaa tggtcgacca gggactcatc aatagagccg cctattccgt ctacctgaac   1740
tcaactgagt ccagcactgc ctcgatcctc ttcggtgcgg ttgaccaaag caaatatacc   1800
ggaagtcttg gcttgcttcc tatcatcaac acggctgctt cctacggtta ccaaaagcct   1860
ctaaggctcc aaatcaccct gtctgccatt acggtcagcg actccagagg acagcaagca   1920
agcattggtt caggagctgc tgctgcactt cttgataccg gaacgacttt gacgtatgct   1980
ccaagcgaga ttgtcgagaa acttgctgaa accctaggct tcgactacag cagctctgtc   2040
ggggcctacg tggcaagatg cagggacgtt gatagctacg ctgtcaactt cgacttccag   2100
ggtaaagtga ttgaagctcc tttgagttcc ttcctgattg ctctgcaaac caactccgga   2160
gaagtttcct cctactgcgc attgggtatt ttctcctctg gagacgaatc cttcacgctc   2220
ggcgatactt tcctgcgaaa cgcctacttt gtggctgacc tcgagggata tcaaatcgct   2280
atagctaacg tgaacctgaa tcctggagcc gagcaaattg aggtcatctc aggcaactcc   2340
attccttctg cttcgtcggt ttccgattac tccaatacct ggggcgcctc tgccaccgct   2400
ttggacactg acaggcctac tactctggga tctgtgactg ctgtgggcga tgaaagagtg   2460
acctcgacca agaaggtttc gagtgtgaag acaagcactt cgtccgggtc cgggtccact   2520
tcggagtcgt ctacgtccag ttcgcattcc agcaatggcc caaggacagt aggctttagt   2580
ttgtgtgccg ttttgtgcgc attcttgatt tctatactag ttgtttgcta gatctgaagt   2640
tctaaggggc tttagtcttc atttatgatt tttttttatt tggaccgcct cgaattgttt   2700
ttccgacggg tctactttaa agctgcaaga tctcgtttag cgtcgtttat ttctcgttcg   2760
tttagtgaca aaaaaacaga aaaaaaaact ataaaagcg gtatataacc tttatatttt   2820
gataaacatg agcagcgaaa ttaagctagc accaaaggat tacgagaagg acaaggagtt   2880
cgccaaggct ctgcatggca aggacgccgc gagcgctaca ggaatgagtg cttgggtgaa   2940
gaaggacaag gaagctcaaa aagtcgcgat ggaaggatat ttcaagcact gggacgggaa   3000
```

```
aaccgacgag gagactgaaa agtcgagact cgaggactac tcgacgctca ccaagcacta    3060
ctacaacctg gtgacggatt tctacgagta tggatgggga tcctcgttcc acttttccag   3120
atactacaag ggagagccat ttagacaagc t                                   3151
```

<210> SEQ ID NO 2
<211> LENGTH: 576
<212> TYPE: PRT
<213> ORGANISM: Hansenula polymorpha

<400> SEQUENCE: 2

```
Met Lys Val Ala Thr Leu Phe Phe Leu Ala Ser Ser Val Cys Val Leu
 1               5                  10                  15

Gly Asp Pro Gln Phe Val Lys Leu Glu Ala Ser Val Leu Arg Gly Ser
            20                  25                  30

Thr Tyr Lys Asp Ser Gln Lys Gly Ala Lys Pro Phe Met Leu Glu Lys
        35                  40                  45

Arg Ala Asp Asp Gly Ser Val Thr Met Glu Leu Gln Asn Ala Gln Ser
    50                  55                  60

Phe Tyr Gln Val Glu Ile Glu Ile Gly Ser Asp Lys Gln Lys Val Gly
65                  70                  75                  80

Val Leu Ile Asp Thr Gly Ser Ser Asp Leu Trp Val Met Asn Ser Asn
                85                  90                  95

Asn Ser Tyr Cys Ser Ser Ser Thr Lys Lys Leu Lys Arg Asp Gly
            100                 105                 110

Pro Ala Asp Ala Leu Gln Lys Gly Arg Asp Leu Ser Asp Leu Tyr Asn
        115                 120                 125

Phe Asn Ser Pro Asn Glu Asp Asn Asn Ala Lys Gly Phe Leu Gly Gly
    130                 135                 140

Trp Gly Asp Leu Thr Thr Val Glu Thr Ala Thr Gln Asp Glu Thr Gln
145                 150                 155                 160

Thr Ala Leu Ala Ala Gln Ala Thr Val Asp Cys Ser Leu Tyr Gly Thr
                165                 170                 175

Phe Asn Pro Ser Thr Ser Asn Ser Phe His Asn Asn Gly Thr Thr Phe
            180                 185                 190

Glu Ile Ser Tyr Ala Asp Arg Thr Phe Ala Arg Gly Thr Trp Gly Tyr
        195                 200                 205

Asp Asp Val Thr Phe Asn Gly Val Thr Val Asn Asp Leu Ser Leu Ala
    210                 215                 220

Val Ala Asp Glu Thr Asp Ser Ser Thr Gly Val Phe Gly Ile Gly Leu
225                 230                 235                 240

Arg Glu Leu Glu Thr Thr Tyr Ser Gly Gly Gly Pro Gln His Tyr Ile
                245                 250                 255

Tyr Asp Asn Leu Pro Phe Lys Met Val Asp Gln Gly Leu Ile Asn Arg
            260                 265                 270

Ala Ala Tyr Ser Val Tyr Leu Asn Ser Thr Glu Ser Ser Thr Ala Ser
        275                 280                 285

Ile Leu Phe Gly Ala Val Asp Gln Ser Lys Tyr Thr Gly Ser Leu Gly
    290                 295                 300

Leu Leu Pro Ile Ile Asn Thr Ala Ala Ser Tyr Gly Tyr Gln Lys Pro
305                 310                 315                 320

Leu Arg Leu Gln Ile Thr Leu Ser Ala Ile Thr Val Ser Asp Ser Arg
                325                 330                 335

Gly Gln Gln Ala Ser Ile Gly Ser Gly Ala Ala Ala Leu Leu Asp
            340                 345                 350
```

```
Thr Gly Thr Thr Leu Thr Tyr Ala Pro Ser Glu Ile Val Glu Lys Leu
        355                 360                 365
Ala Glu Thr Leu Gly Phe Asp Tyr Ser Ser Val Gly Ala Tyr Val
370                 375                 380
Ala Arg Cys Arg Asp Val Asp Ser Tyr Ala Val Asn Phe Asp Phe Gln
385                 390                 395                 400
Gly Lys Val Ile Glu Ala Pro Leu Ser Ser Phe Leu Ile Ala Leu Gln
                405                 410                 415
Thr Asn Ser Gly Glu Val Ser Ser Tyr Cys Ala Leu Gly Ile Phe Ser
                420                 425                 430
Ser Gly Asp Glu Ser Phe Thr Leu Gly Asp Thr Phe Leu Arg Asn Ala
            435                 440                 445
Tyr Phe Val Ala Asp Leu Glu Gly Tyr Gln Ile Ala Ile Ala Asn Val
        450                 455                 460
Asn Leu Asn Pro Gly Ala Glu Gln Ile Glu Val Ile Ser Gly Asn Ser
465                 470                 475                 480
Ile Pro Ser Ala Ser Val Ser Asp Tyr Ser Asn Thr Trp Gly Ala
                485                 490                 495
Ser Ala Thr Ala Leu Asp Thr Asp Arg Pro Thr Thr Leu Gly Ser Val
                500                 505                 510
Thr Ala Val Gly Asp Glu Arg Val Thr Ser Thr Lys Lys Val Ser Ser
                515                 520                 525
Val Lys Thr Ser Thr Ser Ser Gly Ser Gly Ser Thr Ser Glu Ser Ser
        530                 535                 540
Thr Ser Ser Ser His Ser Ser Asn Gly Pro Arg Thr Val Gly Phe Ser
545                 550                 555                 560
Leu Cys Ala Val Leu Cys Ala Phe Leu Ile Ser Ile Leu Val Val Cys
                565                 570                 575

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
gaagtgcagc agcagctcct gaacc                                    25

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
ggctgatgac ggctcggtca cgatgg                                   26

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ggacacgcaa gaggtgtctg                                          20
```

<210> SEQ ID NO 6
<211> LENGTH: 40
<212> TYPE: DNA
<213> ORGANISM: Artificial Sequence
<220> FEATURE:
<223> OTHER INFORMATION: primer

<400> SEQUENCE: 6
agctcgctac ccggggatcc gcaactttca ttgtgtcaac         40

<210> SEQ ID NO 7
<211> LENGTH: 40
<212> TYPE: DNA
<213> ORGANISM: Artificial Sequence
<220> FEATURE:
<223> OTHER INFORMATION: primer

<400> SEQUENCE: 7
gcacatcccc ctttcgccag cctcttcggt gcggttgacc         40

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gctcggctcc aggattcagg         20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ggatccccgg gtaccgagct         20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
caccggtagc taatgatccc         20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
cgaacatcca agtgggccga         20

<210> SEQ ID NO 12
<211> LENGTH: 20
<212> TYPE: DNA
<213> ORGANISM: Artificial Sequence
<220> FEATURE:
<223> OTHER INFORMATION: primer

```
<400> SEQUENCE: 12
ctggcgaaag ggggatgtgc                                                    20

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gaattcatga agtgggtaac cttt                                               24

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
taagcctaag gcagcttgac                                                    20

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15
caagctgcct taggcttatg cagctgctcc ccggtg                                  36

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
actagtgatt tatgggtcct cgatg                                              25
```

HANSENULA POLYMORPHA YAPSIN DEFICIENT MUTANT STRAIN AND PROCESS FOR THE PREPARATION OF RECOMBINANT PROTEINS USING THE SAME

TECHNICAL FIELD

The present invention relates to a process for producing a recombinant protein secreted and expressed from methanol-utilizing *Hansenula polymorpha* yeast at a high yield by efficiently preventing decomposition of the recombinant protein.

More preferably, it relates to a process for efficiently producing a recombinant protein by destroying yapsin1 gene of *H. polymorpha* strain to prevent decomposition of the protein containing a basic or dibasic amino acid residue produced in *H. polymorpha*.

More particularly, it relates to a process for producing a recombinant protein in an intact configuration at a high yield in *H. polymorpha* by preventing decomposition of the recombinant protein having a basic or dibasic amino acid residue in the protein, such as human parathyroid hormone, human serum albumin and serum albumin fusion protein, which comprises cloning the HpYPS1 gene encoding *Hansenula polymorpha* aspartic protease type yapsin1, preparing a *H. polymorpha* strain with the defective HpYPS1 gene using the cloned gene and culturing a transformant transformed from the strain as a host.

BACKGROUND ART

Recently, as demand for high-purity protein medicaments is suddenly increased due to increase of incurable diseases and improvement of public medical standard, relative importance of medicinal recombinant proteins in the health-related bioengineering field is highly raised.

Therefore, the frequency of use of yeast which is a monocellular eukaryotic microorganism as a host system for mass-production of a recombinant protein is gradually increased. Particularly, since yeast has the protein secretion route very similar to those of higher animal cells, it is habitually used as a microorganism host system for production of human-derived secretion proteins. Also, since most kinds of yeast normally secret a very small number of proteins out of the cell, advantageously, recombinant proteins secreted from yeast can be readily recovered and purified. In recent, mass-production of serum proteins, vaccines and other various important medical proteins using non-traditional yeasts including *Hansenula polymorpha* and *Pichia pastoris*, other than the traditional yeast *Saccharomyces cerevisiae* has been successively conducted (Gellissen G., Appl. Microbiol. Biotechnol. 54, 741 (2000)).

As a eukaryotic microorganism, yeast secretes proteins by the substantially same method with mammal cells and involves similar protein modification and cleavage procedures. A protein which has undergone the secretion route becomes to have its final 3-dimensional structure at the Endoplasmic reticulum. In case of glycoprotein, N- and O-bonding sugar chains are attached thereto. Subsequently, the protein is transferred to the Golgi apparatus, in which it is further subjected to the protein modification procedures such as trimming of oligosaccharide or protein cleavage, and thereafter, is transferred to different organs, inserted into components of the cell membrane or secreted out of the cell.

As described above, since the protein secretion procedures in yeast involve various kinds of post-translational modification processes, the secretion and production of a foreign protein in yeast may cause many problems. Particularly, when a recombinant protein is secreted and produced in yeast, it is necessary to use an efficient expression and secretion system in order to increase productivity, but is also important to prevent decomposition of the produced and secreted foreign protein. If a recombinant yeast is cultured for a long period of time at a high concentration in a fermenter, proteases which are naturally secreted from the host cell or exist in the cell through cell lysis are released to medium and degrade the produced recombinant proteins, thereby causing reduction in overall productivity of the recombinant proteins. In order to solve this problem, for yeasts including *Saccharomyces cerevisiae, Hansenula polymorpha, Pichia pastoris* and the like, which have been used as recombinant protein expression systems, various protease deficient strains have been developed. Primarily, strains, in which PEP4, PRB1, or CPY genes encoding degradative enzymes existing in yeast vacuole are destroyed (Alvarez et al., J. Biotechnol. 38, 81 (1994); Chen et al., Curr. Genet. 27, 201 (1995); Gleeson et al., Methods Mol. Biol. 103, 81 (1998); Kang et al. In *Hansenula polymorpha* (ed. Gellissen G.) p. 124 (2001)), have been developed. In addition to the vacuole degradative enzymes, kex1Δ strain have been developed, in which KEX1 gene encoding carboxypeptidase α existing in the Golgi apparatus is destroyed. By the kex1Δ strain, C-end decomposition of hirudin in *Saccharomyces cerevisiae* (Hinnen et al., In Gene expression in recombinant microorganisms (ed. Smith A.), p 121 (1995)), of human epidermal growth factor in *Hansenula polymorpha* (Heo et al., Protein expr. purif. 24, 117 (2001)) and of rodent or human endostatin in *Pichia pastoris* (Boehm et al., Yeast 15, 563-567 (1999)) can be significantly reduced.

Recently, yeast aspartic protease type yapsins having activity to recognize and cut basic amino acids existing as a single or a pair in *Saccharomyces cerevisiae* have been identified, which are novel proteases existing in the cell membrane (Egel-Mitani et al., Yeast 6, 127-137 (1990)). Yapsin1 (also previously known as yeast aspartic protease 3 (YAP3)) was firstly known to the public among the yeast aspartic proteases, and yapsin2 (also previously known as MKC7) was known thereafter (Komano and Fuller, Proc. Natl. Acad. Sci. USA 7, 92, 10752-10756 (1995)). By the *Saccharomyces cerevisiae* genome information which has been recently disclosed to the public, additional genes encoding at least 5 yapsin type protease presumed to have similar functions, such as yapsin3, yapsin6 and yapsin7, have been reported to exist so far (Olsen et al. Biochem. J. 339, 407-411 (1999)). Though the physiological functions of these yapsins are not clearly shown, as the number of study cases reporting that target recombinant proteins which are intended to secret and produce in *S. cerevisiae* are cleaved by the protease activity of yapsin is increased, yapsin deficient yeast strains attract public attention as an useful strain for production of a recombinant protein, particularly a foreign peptide having a basic amino acid. Recombinant proteins which have been reported to have problems of being cleaved by yapsins in secretion and production in *S. cerevisiae*, till now, include human serum albumin (Kerrywilliams et al., Yeast 14, 161-169 (1998)), human parathyroid hormone (Kang et al., Appl Microgiol Biotechnol., 50, 187-192 (1998)); Korean Patent Registration No. 0246932 (publicated on Dec. 8, 1999)), insect diuretic hormone (Copley et al., Biochem J., 330, 1333-1340 (1998)), glucagon and glucagon-like peptide (Egel-Mitani et al., Enzyme Microb Technol. 26, 671-677 (2000): U.S. Pat. No. 6,110, 703) and human elafin precursor (Bourbonnais et al., Protein Exp. Purif. 20, 485 (2000)). Meanwhile, considering that YPS1 deficient *S. cerevisiae* strain shows a considerable progress in decomposition of hPTH at the last stage of the cultivation using a fermenter, the present inventors have developed *S. cerevisiae* yapsin multiple deficient mutant strain (yps1Δ/yps2Δ/yps3Δ), in which the YPS2 and YPS3 genes coding for yapsin2 and yapsin3 are removed. As a result, we have obtained an excellent result of preventing 90% or more of degradation of human parathyroid hormone observed in a high-concentration cultivation (Korean Patent Application No. 2000-51267 and International Application No. PCT/KR01/01447).

*H. polymorpha*, one of methanol-utilizing yeasts, is in the spotlight as a very useful yeast host for mass production of recombinant proteins since it has advantages in that strong and controllable promoters are developed, alike *Pichia pastoris*, and a foreign gene can be multiply introduced into the host chromosome (Faber et al., Yeast 11, 1331 (1995)). Up to date, various kinds of foreign proteins have been expressed and the expression levels often reached over 1 g/L in case of high-concentration cultivation using a fermenter. Particularly, it has been reported that when recombinant phytase is secreted and produced, the expression level is about 13.5 g/L (Mayer et al., Biotechnol. Bioeng. 63, 373-381 (1999)). Therefore, the *H. polymorpha* expression system becomes distinguished as one of the most potential systems among several presently available eukaryotic cell expression systems. Especially, since some of the recombinant proteins which have been produced in the initial stage in *H. polymorpha* have already passed clinical trials and are on the market (ex., hepatitis B vaccine) or in the product development phase (ex., hirudin), *H. polymorpha* is considered as a suitable expression system for production of a recombinant protein to be developed as an medicament (Gellissen G., Appl Microbiol Biotechnol. 54 741-750 (2000)). Also, as recently getting into the post-genome era, there is an increased need for a high-efficiency expression system for functional analysis of novel genes, and thus it is expected that an expression system using *H. polymorpha* would bear a great part in functional and structural analysis of novel proteins as well as mass production of useful proteins derived from higher eukaryotic cells.

DISCLOSURE OF INVENTION

Therefore, the present invention has been made to develop a high-efficiency *H. polymorpha* expression system by solving the problems related to undesired cleavage and decomposition of a recombinant protein by an yapsin type protease, and it is an object of the present invention to provide a technology for secreting and producing a recombinant protein in an intact configuration at a high efficiency by preventing cleavage and decomposition of the recombinant protein expressed in *H. polymorpha*, in which the HpYPS1 gene encoding *H. polymorpha* yapsin1 is cloned, the cloned gene is used to prepare HpYPS1 gene deficient mutant strain and the prepared mutant strain is used as a recombinant protein expression host.

In accordance with an aspect, the present invention provides a gene sequence encoding yapsin1(HpYPS1) of *H. polymorpha* strain by probing yapsin protease genes in *Hansenula polymorpha* strain, as identified in *S. cerevisiae*.

Also, in further aspect, the present invention provides a yapsin1 polypeptide having *Hansenula polymorpha* strain-derived aspartic protease activity.

Also, in another aspect, the present invention provides a secretion signal gene sequence and a peptide sequence of HpYPS1 polypeptide for secretion of a foreign protein recombinantly produced in *Hansenula polymorpha* strain.

According to yet another aspect, in order to develop a *Hansenula polymorpha* strain capable of secreting and producing a recombinant protein in an original configuration at a high efficiency, the present invention provides an expression system for secretion and production of a recombinant protein at a high efficiency in *Hansenula polymorpha* by cloning the above-described *Hansenula polymorpha* yapsin protease gene and deleting the cloned gene to minimize the decomposition of the recombinant protein in *Hansenula polymorpha*.

In order to accomplish the above objects, the present inventors have developed a *Hansenula polymorpha* mutant strain (hpyps1Δ), in which the HpYPS1 gene is deleted, by cloning the HpYPS1 gene encoding *Hansenula polymorpha* yapsin1 and subjected the resulting HpYPS1 gene to a functional analysis. Consequently, we have formed a method for increasing productivity of a recombinant protein by using the *Hansenula polymorpha* mutant strain as a host strain to express the protein containing a basic or dibasic amino acid residue in the protein, including human parathyroid hormone, human serum albumin and human serum albumin fusion protein, thereby significantly reducing the decomposition of the recombinant protein expressed and secreted in *H. polymorpha*.

BRIEF DESCRIPTION OF DRAWINGS

Further objects and advantages of the invention can be more fully understood from the following detailed description taken in conjunction with the accompanying drawings in which:

FIG. 1 shows the nucleotide sequence of gene HpYPS1 encoding *H. polymorpha* yapsin1 and the expected amino acid sequence (①: a signal sequence, ②: the expected GPI anchor, ③: a hydrophobic amino acid-golgi membrane fixing domain);

FIG. 2 shows the comparison of the amino acid sequence between *H. polymorpha* yapsin1 and *S. cerevisiae* yapsin type proteases;

FIG. 7A shows the result of Southern blot to examine the expression vector insertion sites and the number of copies by isolating chromosomes of the *Hansenula polymorpha* wild type and the mutant strain hpyps1Δ transformed with the vector pMOXhPTH;

FIG. 7B shows the results of SDS-polyacrylamide electrophoresis of yeast culture supernatants, followed by staining, to compare the expression and decomposition aspects of recombinant human parathyroid hormone in the transformants of *H. polymorpha* wild type and hpyps1Δ mutant strain;

FIG. 8A shows the results of comparison of the expression and decomposition aspects of recombinant human serum albumin when the *H. polymorpha* wild type strain and the HpYPS1 gene-deleted hpyps1Δ mutant strain are used as a host, in which yeast culture supernatants are analyzed by SDS-polyacrylamide electrophoresis, followed by staining;

FIG. 8B shows the results of comparison of the expression and decomposition aspects of recombinant human serum albumin when the *H. polymorpha* wild type strain and the HpYPS1 gene-deleted hpyps1Δ mutant strain are used as a host, in which yeast culture supernatants are analyzed by Western blotting;

BEST MODE FOR CARRYING OUT THE INVENTION

Figure 3:
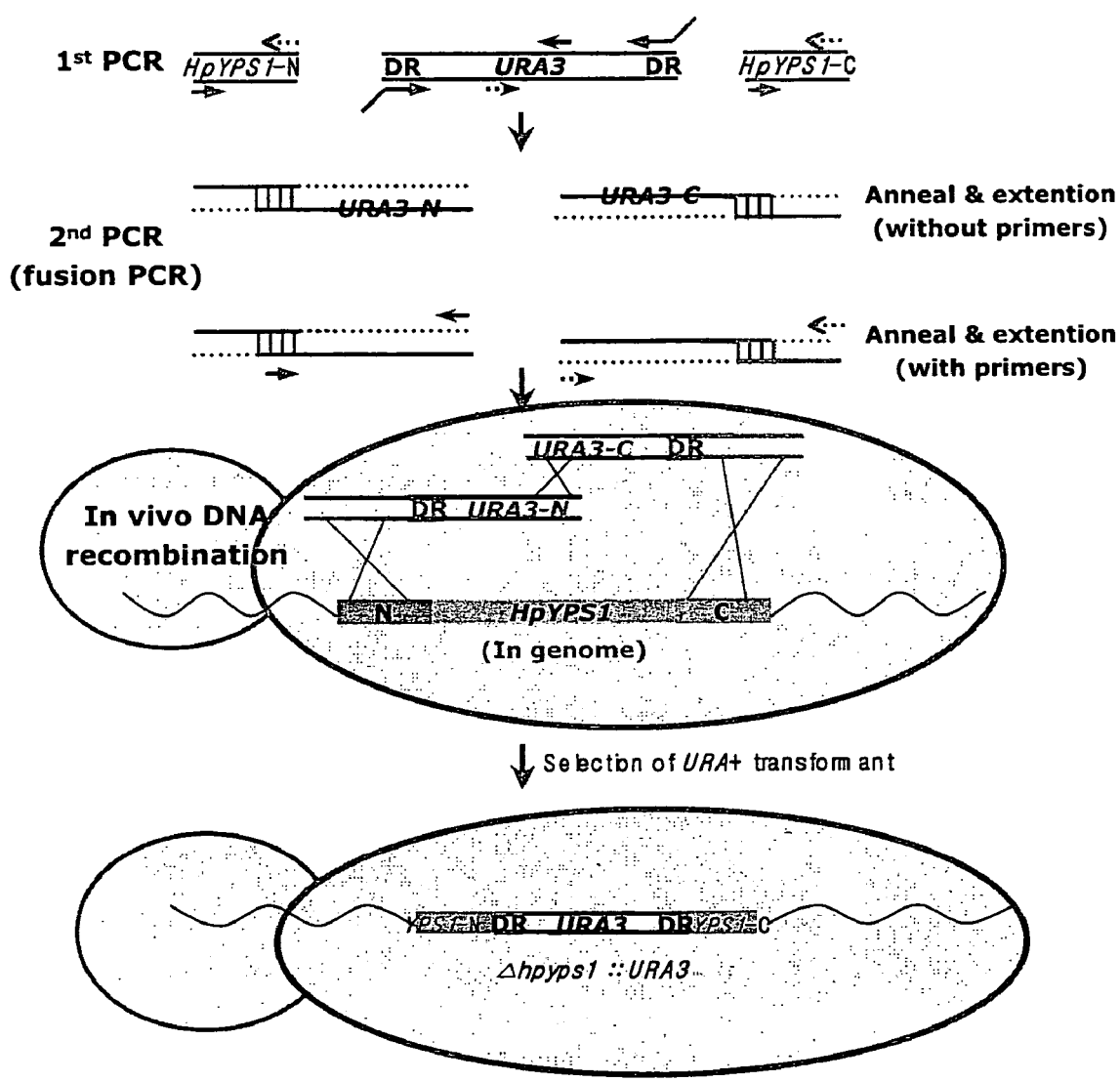
FIG. 3 is the result of the functional complementation experiment showing that temperature sensitivity of *Saccharomyces cerevisiae* yapsin multiple deficient mutant strain is recovered as the *Hansenula polymorpha* yapsin1 gene HpYPS1 is expressed.

*H. polymorpha* is a class of yeast which can use methanol as a carbon source and energy source. According to the present invention, there is provided a *H. polymorpha* mutant strain with yapsin enzyme destroyed, based on the fact that when *H. polymorpha* is used in a method for producing a foreign protein, the yield of the foreign protein is reduced since the produced foreign protein is decomposed by yapsin enzyme which is an aspartic protease existing in the yeast.

As described herein, the yapsin enzyme family, which is a sub-family of aspartic proteases, has an ability to specifically cleave a basic or dibasic amino acid residue of a protein. This is a difference from other aspartic proteases cleaving hydrophobic residues.

The present inventors have obtained a segment showing similarity with the *S. cerevisiae* yapsin1 encoding gene (YPS1) from the PCR-amplified chromosomes derived from *H. polymorpha* and conducted researches and studies on functions of the segment.

As a result, the segment was identified as HpYPS1 gene of *H. polymorpha*. Further, we have prepared a *Hansenula polymorpha* mutant strain having the HpYPS1 gene destroyed and confirmed that a foreign protein can be produced from the strain at a high yield. Thus, the present invention has been completed.

In one aspect, the present invention provides a nucleic acid molecule comprising the sequence shown in FIG. 1.

More particularly, the present invention provides a nucleic acid molecule comprising the sequence encoding *Hansenula polymorpha* yapsin1 shown in FIG. 1.

In another aspect, the present invention provides a polypeptide comprising the amino acid sequence shown in FIG. 1.

More particularly, the present invention provides a polypeptide comprising the amino acid sequence of *Hansenula polymorpha* yapsin1(HpYPS1) shown in FIG. 1.

In another aspect, the present invention provides a secretion signal gene sequence and a peptide sequence of HpYPS1 polypeptide for secretion of a foreign protein recombinantly produced in *Hansenula polymorpha* strain, shown as ① in FIG. 1.

In another aspect, the present invention provides a *H. polymorpha* mutant strain having reduced yapsin activity by mutation of the HpYPS1 gene encoding *H. polymorpha* yapsin1.

In another aspect, the present invention provides a recombinant *H. polymorpha* strain expressing a foreign protein by introducing a gene encoding the foreign protein into the *H. polymorpha* mutant strain.

In another aspect, the present invention provides a process for preparing a foreign protein comprising culturing a recombinant *H. polymorpha* strain under conditions to express the foreign protein and isolating the foreign protein from the culture.

More particularly, the present invention provides a process for secreting and producing a recombinant protein in *Hansenula polymorpha* using a yeast strain lacking the HpYPS1 gene for a yapsin type protease as a host. The present invention comprises the steps of: cloning gene the HpYPS1 encoding *H. polymorpha* protease yapsin1; functional analyzing the resulting *H. polymorpha* HpYPS1 gene by temperature sensitivity complementation experiment of a *Saccharomyces cerevisiae* yapsin multiple deficient mutant strain; preparing a hpyps1Δ mutant strain with the HpYPS1 gene destroyed in *Hansenula polymorpha*, followed by analysis of yapsin activity; and preparing a recombinant *Hansenula polymorpha* strain hpyps1Δ-pMOXhPTH to express and secrete human parathyroid hormone, a recombinant *Hansenula polymorpha* strain hpyps1Δ-pYHSA12 to express and secrete human serum albumin, or recombinant a *Hansenula polymorpha* strain hpyps1Δ-pYHSA13-TIMP2 to express and secrete a TIMP2 protein fused with human serum albumin recombinant protein using the *H. polymorpha* mutant strain hpyps1Δ as a host, followed by analysis of decomposition level of the recombinant protein. Therefore, the present invention relates to a method for efficiently producing a recombinant protein by preventing degradation of the recombinant protein expressed from methanol utilizing yeast *H. polymorpha*, which comprises cloning the HpYPS1 gene encoding *H. polymorpha* aspartic protease type yapsin, preparing a *H. polymorpha* strain with the HpYPS1 gene deficient using the cloned gene, and culturing a transformant transformed from the strain as a host to minimize degradation of the recombinant protein, thereby producing the recombinant protein in an intact configuration at a high yield.

The sequence of the *H. polymorpha* YPS1 gene (HpYPS1) (SEQ ID NO: 1) cloned according to the present invention was deposited in GenBank under Accession No. AF493990. Also, the HpYPS1 gene encoding *H. polymorpha* protease yapsin1 was deposited in an international depository authority, the Korean Collection for Type Cultures, 52, Oun-dong, Yusong-Ku, Taejon 305-333, Republic of Korea, on the date of Jun. 18, 2002 and assigned Accession No. KCTC 10285BP. Further, the hpyps1Δ mutant strain having the HpYPS1 gene destroyed in *H. polymorpha* was deposited in an international depository authority, the Korean Collection for Type Cultures, 52, Oun-dong, Yusong-Ku, Taejon 305-333, Republic of Korea, on the date of Jun. 18, 2002 and assigned Accession No.

KCTC 10281BP. In an embodiment, the recombinant *H. polymorpha* strain hpyps1Δ-pMOXhPTH expressing and secreting human parathyroid hormone was deposited in an international depository authority, the Korean Collection for Type Cultures, 52, Oun-dong, Yusong-Ku, Taejon 305-333, Republic of Korea, on the date of Jun. 18, 2002 and assigned Accession No. KCTC 10282BP. In another embodiment, the recombinant *H. polymorpha* strain hpyps1Δ-pYHSA12 expressing and secreting human serum albumin was also deposited in an international depository authority, the Korean Collection for Type Cultures, 52, Oun-dong, Yusong-Ku, Taejon 305-333, Republic of Korea, on the date of Jun. 18, 2002 and assigned Accession No. KCTC 10283BP. In addition, the recombinant *H. polymorpha* strain hpyps1Δ-pYHSA13-T2 expressing and secreting albumin-TIMP2 fusion protein was deposited in an international depository authority, the Korean Collection for Type Cultures, 52, Oun-dong, Yusong-Ku, Taejon 305-333, Republic of Korea, on the date of Jun. 23, 2003 and assigned Accession No. KCTC 10485BP.

Now, the present invention will be explained in detail by the following examples. However, it should be understood that the following examples are only for illustrative purposes and are not intended to limit the scope of the invention.

EXAMPLE 1

Cloning of *Hansenula polymorpha* yapsin1 Gene HpYPS1 and Analysis of the Sequence In order to find a gene encoding yapsin1 in *H. polymorpha*, a pair of synthetic oligonucleotides (5'-GAAGTG-CAGCAGCAGCTCCTGAACC-3'; SEQ ID NO: 3, 5'-GGCTGATGACGGCTCGGTCACGATGG-3'; SEQ ID NO: 4) were prepared, on the basis of information on *H. polymorpha* random sequenced tags described in Blandin et al., (FEBS Lett. 487, 76, (2000). By PCR (Polymerase Chain Reaction) using the prepared oligonucleotides as primers, a 0.88 kb DNA segment was amplified from *H. polymorpha* DL-1L derived chromosome. Then, Southern blotting was conducted using the amplified DNA segment as a probe. Based on the result of the Southern blot, 3.5 kb HindIII DNA segments was extracted from *H. polymorpha* chromosomal DNA to prepare a genome library, which was transformed into *E. coli*. A DNA segment reactive with the DNA probe was isolated by colony PCR and subjected to DNA sequencing to identify a DNA segment comprising ORF (Open Reading Frame) with a size of 1728 bp showing a high similarity with the *Saccharomyces S. cerevisiae* YPS1 gene (FIG. 1). The *H. polymorpha* YPS1 gene (HpYPS1) product has a signal sequence of 1-17 amino acids at its N-end and a region of 556-575 amino acids, presumed as a domain which can be anchored on the membrane of Golgi apparatus, as reported on *S. cerevisiae* yapsin1.

Also, it has structural features, by which a glycosylphosphatidylinositol anchor can be attached thereto, as in *S. cerevisiae* yapsins (FIG. 1). *H. polymorpha* yapsin1 (SEQ ID NO: 2) shows a homology of 36% and a high similarity of 52% with *S. cerevisiae* yapsin1 and a homology of 30% or more with other yapsin proteases (FIG. 2, Table 1).

TABLE 1

Homology and similarity of HpYPS1 and ScYPS genes

| | ScYPS1 | ScYPS2 | ScYPS3 | ScYPS6 | ScYPS7 |
|---|---|---|---|---|---|
| HpYPS1 | 36%(52%) | 31%(49%) | 30%(44%) | 26%(44%) | 29%(34%) |

* Parenthesized number is similarity

EXAMPLE 2

Functional Analysis of the *Hansenula polymorpha* HpYPS1 Gene

In case of the traditional yeast *Saccharomyces cerevisiae*, it has been reported that YPS1/YPS2 double deficient mutant strain derived from *S. cerevisiae* W303 strain as a parental strain shows a such high temperature sensitivity that it cannot grow at 37° C. (Komano and Fuller, Proc. Natl. Acad. Sci. USA 7, 92, 10752-10756 (1995)). Also, SLH18 (yps1Δ/yps2Δ/yps3Δ) strain (Korean Patent Registration No. 10-0386836), which is a yapsin multiple deficient mutant strain having three genes of YPS1/YPS2/YPS3 destroyed, prepared using *Saccharomyces cerevisiae* L3262 as a parental strain by the present inventors, was found to show temperature sensitivity at a high temperature. As a method for functional analysis of the *Hansenula polymorpha* yapsin1 gene HpYPS1, a functional complementation experiment was conducted by transforming the HpYPS1 gene into the above-described *Saccharomyces cerevisiae* multiple yapsin mutant strain according to the lithium chloride-DMSO method (Hill et al., Nucleic Acid Res., 19, 5791 (1991)) to examine whether the expression of *Hansenula polymorpha* yapsin1 gene could restore temperature sensitivities of the *Saccharomyces cerevisiae* multiple yapsin mutant strains. In order to express the HpYPS1 gene in *Saccharomyces cerevisiae*, 3.2 kb DNA segment including the HpYPS1 gene was inserted into the *Saccharomyces cerevisiae* multicopy vector YEp352 (Hill et al., Yeast 2, 163, (1986)) to generate YEp-HpYPS1.

As shown in FIG. 3, the *Saccharomyces cerevisiae* yapsin multiple deficient mutant strains transformed with the YEp352-HpYPS1 vector containing the HpYPS1 gene showed the same growth with the wild type strain at 37° C., while the yapsin multiple deficient mutant strain transformed with only YEp352 vector, used as control, did not grow at 37° C. From these results, it was proved that the temperature sensitivity due to the multiple deletion of *Saccharomyces cerevisiae* yapsin genes can be overcome by the expression of the *Hansenula polymorpha* yapsin 1 gene. Thus, there was provided a basis supporting that the *H. polymorpha* gene HpYPS1 cloned according to the present invention is a functional homologue of yapsin gene of *S. cerevisiae*.

EXAMPLE 3

Preparation of the HpYPS1 Gene-Deficient Strain and Analysis of Yapsin Activity

Using the HpYPS1 gene prepared above, a *H. polymorpha* yapsin deficient mutant strain hpyps1Δ was synthesized and assayed for change in its protein decomposition activity by yapsin. In order to prepare a mutant strain having the deletion of the HpYPS1 gene encoding *Hansenula polymorpha* yapsin 1, a fusion PCR (Oldenhurg et al., Nucleic Acid Res. 25, 451, (1997)) was conducted on *H. polymorpha* chromosomal DNA using primers described in Table 2. The resulting DNA segment was transformed into *Hansenula polymorpha* DL1-LdU (leu2Δura3::lacz; Kang et al., In *Hansenula polymorpha*:Biology and Application (Ed. G. Gellissen), pp 124 (2002)) strain to induce in vivo homologous recombination, thereby attempting deletion of the gene. More specifically, a primary PCR was firstly conducted to obtain the N-ends, C-ends of HpYPS1 gene and URA3 gene. Then, a secondary fusion PCR was conducted to fuse the N-end and C-end of HpYPS1 gene with the N-end and C-end of URA3 gene, respectively. The two DNA segments thus obtained were introduced to yeast cells.

Figure 4:
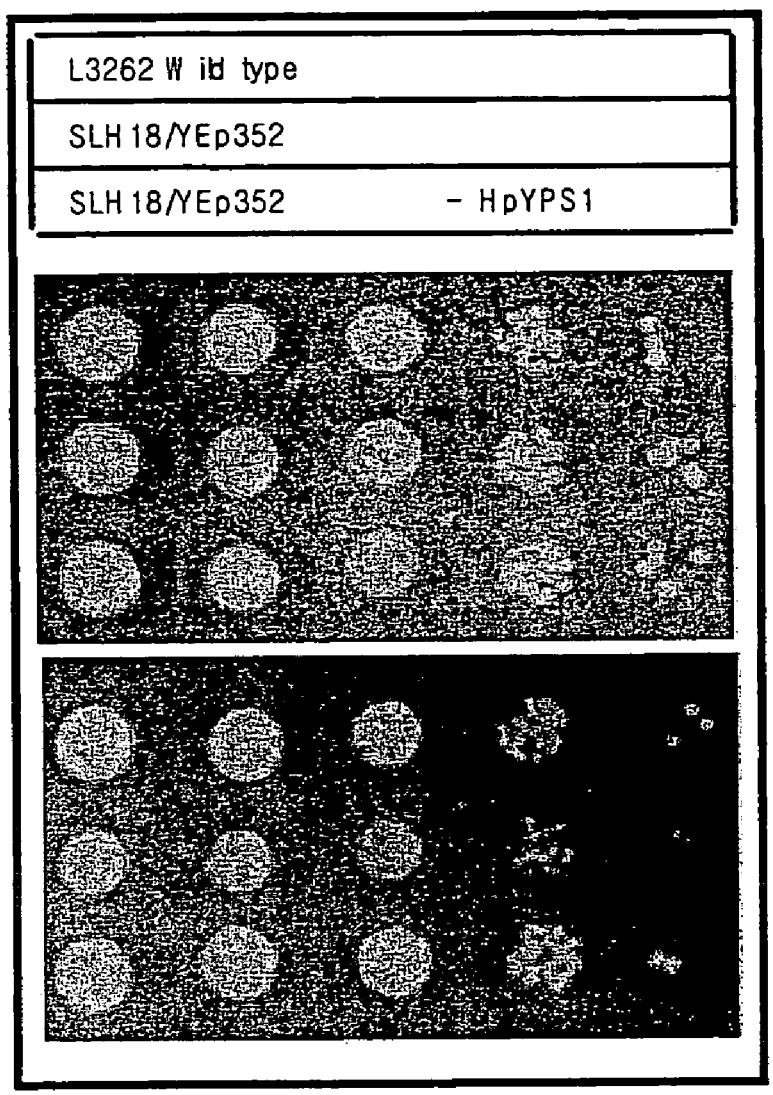
FIG. 4 is a schematic view showing the procedures for preparing a *Hansenula polymorpha* yapsin1 gene-disrupted mutant strain hpyps1Δ.

Using URA3 as a selection marker, viable transformants were selected in a minimal medium lacking uracil. Construction of the hpyps1Δ strain (leu2Δura3::lacz yps1:: URA3), which is a *H. polymorpha* mutant strain having the deleted HpYPS1 gene, was confirmed by PCR, which generated the DNA segments with different sizes between the wild type strain and the mutant strain. (FIG. 4).

For the comparison of the yapsin activity of *H. polymorpha* hpyps1Δ mutant strain prepared above with that of the wild type strain, each of the two strains was cultured for 10 hours in YPD medium (1% yeast extract, 2% peptone, 2% glucose) using human parathyroid hormone (hPTH) as a substrate. The resulting yeast culture supernatant was analyzed for its protein degradation activity. 20 μl of the yeast culture supernatant which had been diluted ¼ was mixed with hPTH (about 1.6 μg) acting as a substrate. The reaction was incubated for 2 hours, 4 hours and 6 hours at 37° C. Each product was loaded on SDS-polyacrylamide gel to analyze the degradation level of hPTH by the yapsin activity.

Figure 5:
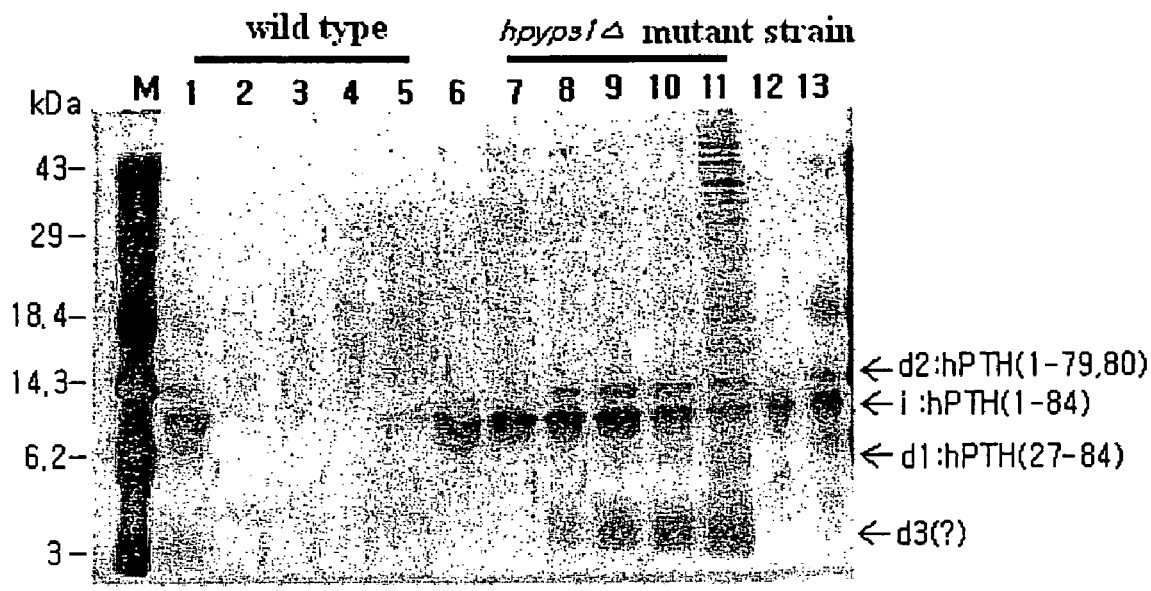
FIG. 5 shows the results of comparison of protease activity in the culture supernatants of the *H. polymorpha* wild type and the yapsin1-deficient hpyps1Δ mutant strain, in which human parathyroid hormone is used as a substrate.

As shown in FIG. 5, in the culture fluid of the wild type, it was already hard to observe hPTH remaining in the culture supernatant after 2 hour cultivation, while in the culture supernatant of hpyps1Δ mutant strain, a substantial amount of hPTH was observed, though the amount was somewhat reduced as the reaction time became longer.

This suggests that the culture supernatant of hpyps1Δ, the *Hansenula polymorpha* HpYPS1 deficient mutant strain, had a significantly reduced hPTH degradation activity, as compared to the culture supernatant of the wild type strain. Such result shows the same result with the previous study performed on *S. cerevisiae* YPS1 deficient mutant strain (Kang et al., Appl Microbiol Biotechnol. 50, 187, (1998)) and thus, supports the fact that HpYPS1 is a gene encoding yapsin protease of *H. polymorpha* and the HpYPS1 deficient mutant strain developed according to the present invention has the yapsin activity reduced.

TABLE 2

Primers used in fusion PCR for destruction of HpYPS1 gene

| Primer | Sequence | SEQ ID NO: |
|---|---|---|
| YPS(NF) | 5'-GGACACGCAAGAGGTGTCTG- 3' | 5 |
| YPS(NR + rp) | 5'-AGCTCGCTACCCGGGGATCCGCAACTT TCATTGTGTCAAC- 3' | 6 |
| YPS(CF + rp) | 5'-GCACATCCCCCTTTCGCCAGCCTCTTC GGTGCGGTTGACC- 3' | 7 |
| YPS(CR) | 5'-GCTCGGCTCCAGGATTCAGG- 3' | 8 |
| URA3 N-S | 5'-GGATCCCCGGGTACCGAGCT- 3' | 9 |
| URA3 N-A | 5'-CACCGGTAGCTAATGATCCC- 3' | 10 |

TABLE 2-continued

Primers used in fusion PCR for destruction of HpYPS1 gene

| Primer | Sequence | SEQ ID NO: |
|---|---|---|
| URA3 C-S | 5'-CGAACATCCAAGTGGGCCGA- 3' | 11 |
| URA3 C-A | 5'-CTGGCGAAAGGGGGATGTGC- 3' | 12 |

EXAMPLE 4

Figure 6:
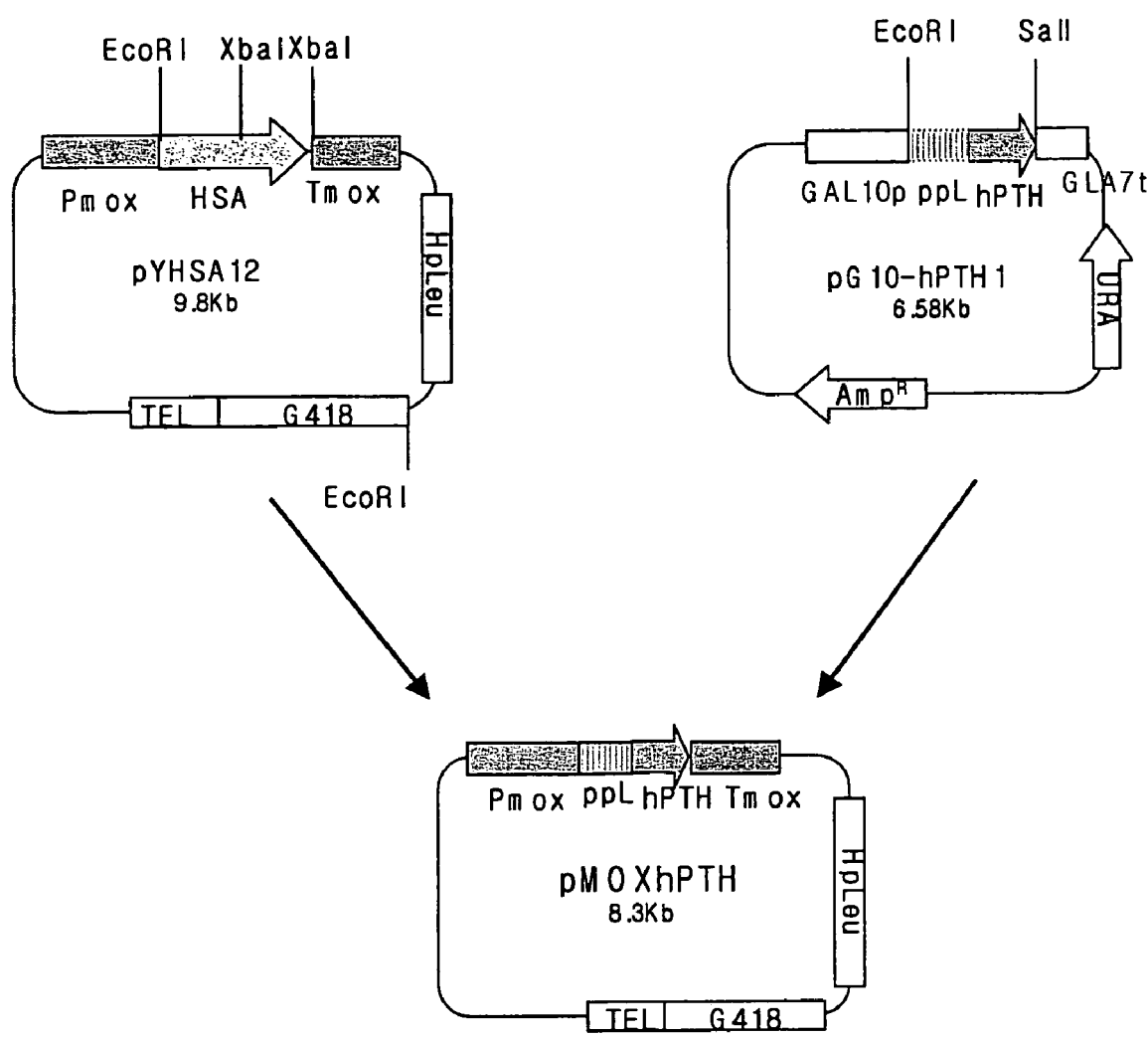
FIG. 6 shows a schematic view of the procedures to construct the human parathyroid hormone expression vector pMOXhPTH for *H. polymorpha;*

Construction of the Recombinant *H. polymorpha* Strain Expressing hPTH and Analysis of the hPTH Expression In order to practically express and secret human parathyroid hormone (hPTH) in *H. polymorpha*, pMOXhPTH, a human parathyroid hormone expression vector for *H. polymorpha* was prepared according to a method shown in FIG. 6. Thus, the 0.53 kb EcoRI/SalI segment containing the hPTH cDNA fused with a MFα signal sequence was prepared from pG10-hPTH, a hPTH expression vector for *S. cerevisiae* (Chung et al., Biotechnol Bioeng. 57, 245, (1998)) and the 7.8 kb XbaI/EcoRI segment having the albumin cDNA removed was prepared from pYHSA12, a human serum albumin expression vector for *H. polymorpha* (Kang et al., Biotechnol Bioeng. 76, 175, (2001)).

The two DNA segments were joined to generate pMOXhPTH. The resulting vector pMOXhPTH was introduced into the *H. polymorpha* hpyps1Δ mutant strain and the wild type strain, and viable transformants were selected in minimal medium lacking leucine. At every 24 hours after inoculation, Leu⁺ transformants were transferred to liquid minimal selective medium lacking leucine 5 times to stabilize the Leu⁺ transformants (Sohn et al., Appl Microbiol Biotechnol. 51, 800, (1999)). The culture broth of the Leu⁺ transformants obtained as described above was plated onto minimal media containing G418 at various concentrations and cultured at 37° C. DNA was isolated from each of the resulting colonies and subjected to Southern blot analysis using the 1.5 kb *H. polymorpha* LEU2 gene as a hybridization prove according to the method described by Sambrook et al. (Molecular cloning Cold Spring Harbor Laboratory Press, 1989) to confirm insertion into the chromosome of the expression vector (FIG. 7A). The *H. polymorpha* LEU2 gene used as a probe was prepared by labeling with digoxigenin using the non-radioactive DNA labeling and detection kit. As having been expected, in the transformants selected on the medium containing a high G418 concentration, multiple integration of the vector pMOXhPTH was observed. Upon comparison of intensity between the LEU2 gene signal on the chromosome and the LEU2 gene signal on the inserted vector, it was presumed that about 5 to 6 copies at most had been inserted.

Some tranformants (a, b, c, d, e and f) of the recombinant yeast strains which had been confirmed to have the hPTH expression vector integrated into the chromosome were inoculated into YPM medium (1% yeast extract, 2% peptone, 2% methanol) and cultured at 37° C. Yeast culture supernatants obtained at 12 hours and 24 hours after initiation of the cultivation were treated with TCA (trichloroacetic acid). The proteins secreted out of the cells were concentrated to 1/20 of the initial volume and electrophoresed on 15% SDS-polyacrylamide gel, followed by staining with Coomassie Brilliant Blue R-250 (FIG. 7B).

When the hPTH secreted in *polymorpha* wild type was compared with that secreted in the hpyps1Δ mutant strain, only a trace of decomposition product (d1) was observed in the culture supernatant obtained from the wild type and hPTH of a whole size (i) was hardly observed, since most of hPTH was decomposed. On the other hand, secretion of hPTH of a whole size was clearly observed in the culture supernatant obtained from the hpyps1Δ mutant strain at 12 hours after cultivation. From these results, it was shown that the hpyps1Δ mutant strain having the yapsin1 gene destroyed is a more useful strain as a host for secretory expression of recombinant hPTH, as compared to the wild type, since the decomposition of the recombinant parathyroid hormone is considerably inhibited by the reduction of yapsin activity, although hPTH of a whole size was reduced in the hpyps1Δ mutant strain while the band (d2), it is presumed, of hPTH having the C-end decomposed was observed, as the cultivation time became longer.

EXAMPLE 5

Analysis of Expression and Secretion of Recombinant Human Serum Albumin in *H. polymorpha* HpYPS1 Gene Deficient Mutant Strain The human serum albumin (HSA) expressed in *S. cerevisiae* is secreted as an intact form of 67 kDa, however some recombinant HSA in a decomposed form of 45 kDa also have been observed. It was reported that degradation of HSA secreted to yeast cell culture supernatant, particularly production of a decomposition product with a size of 45 kDa was reduced when a *S. cerevisiae* strain with the yapsin1 gene destroyed was used as a host (Kerry Williams et al., Yeast 14, 161, (1998)). In order to analyze the expression and degradation aspects of recombinant HSA in the *H. polymorpha* HpYPS1 gene deficient mutant strain developed according to the present invention, the hpyps1Δ mutant strain was transformed with an expression vector pYHSA12 (Kang et al., Biotech Bioeng. 76, 175, (2001)), in which the MOX promoter and the HSA cDNA were joined to a vector for copy-number controlled gene integration using the LEU2 gene and G418 resistance gene as selective markers. Recombinant *H. polymorpha* wild type strain and hpyps1Δ mutant strain were cultured in YPGM medium (1% yeast extract, 2% peptone, 1% glycerol, 2% methanol). Each of the culture supernatants thus-obtained was loaded on SDS-polyacrylamide gel, followed by staining with silver nitrate, or transferred to a nitrocellulose membrane, followed by Western blot by HSA antibody to examine expression and degradation aspects of HSA. As shown in FIG. 8, it was observed that more HSA was secreted in the hpyps1Δ mutant strain than the wild type strain, particularly after cultivation for 24 hours. Though the overall degradation of albumin was not significantly inhibited, it was shown that degradation product with a size of 45 kDa was apparently reduced in the hpyps1Δ mutant strain, as compared to the wild type, as observed particularly in *S. cerevisiae*. Considering cultivation in a high concentration fermenter, production of 45 kDa degraded HSA product presents more serious problems, it is expected that an albumin production system using the hpyps1Δ mutant strain as a host can increase production of albumin due to a remarkable reduction in degradation of albumin, as compared to an production system using the wild type strain as a host.

EXAMPLE 6

Figure 9:
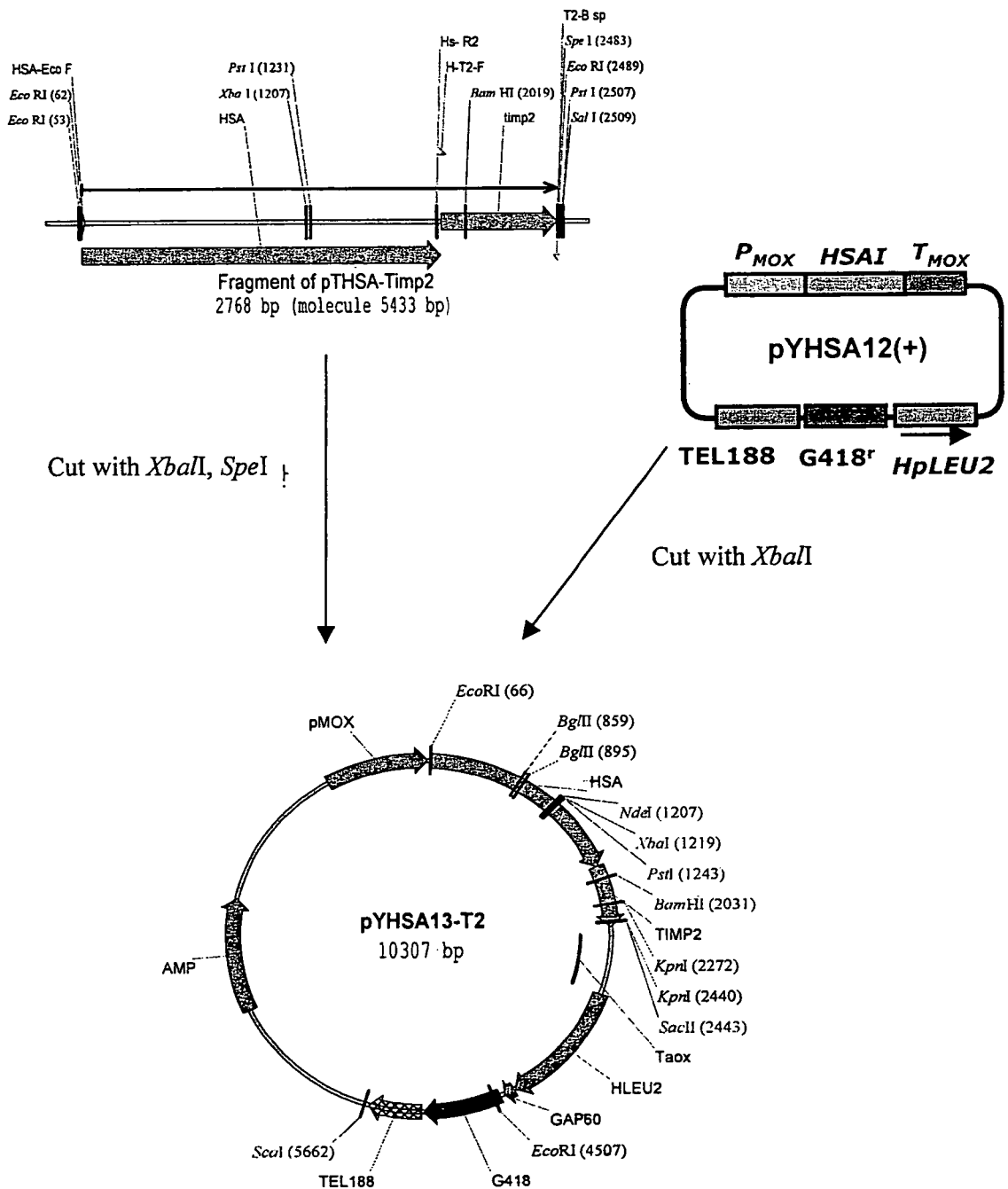
FIG. 9 shows a schematic view of the procedures for constructing the albumin-TIMP2 fusion protein expression vector pYHSA13-T2 for *Hansenula polymorpha*.

Analysis of Expression and Secretion of Recombinant Albumin Fusion TIMP2 (HSA-TIMP2) in *H. polymorpha* HpYPS1 Gene Deficient Mutant Strain As a part of a method to increase blood persistence of a protein therapeutic agent, researches to develop a technology to increase in vivo half-life of a medical protein by expressing a recombinant protein in a form fused to albumin, a blood protein which has a long stability, are in the spotlight (Smith et al., Bioconjugate Chem. 12, 750-756, (2001); Sheffield et al. Blood Coagul Fibrinol. 12, 433-443, (2001)). The present inventors also have developed a recombinant TIMP-2 having in vivo stability significantly increased by expressing TIMP-2, which attracts public attention as a next generation anti-angiogenesis agent and anti-tumor agent, as a recombinant protein fused to albumin in *S. cerevisiae* (Korea Patent Registration No. 10-2001-0027823, International Application No. PCT/KR03/00015). In order to analyze the expression and e decomposition aspect of the recombinant HSA-TIMP2 in a form fused to albumin in the *H. polymorpha* HpYPS1 gene deficient mutant strain (hpyps1Δ) developed according to the present invention, YHSA13-T2, a HSA-TIMP2 expression vector for *H. polymorpha* was prepared according to the method shown in FIG. 9. That is, the DNA fragments encoding HSA and TIMP2 were prepared using the PCR primers described in Table 3. Fusion PCR was conducted using the prepared genes in a ratio of 1:1 to prepare the 2.4 kb HSA-TIMP2 DNA segment comprising HSA (1.8 kb) and TIMP2 (0.586 kb), which are connected to each other. The resulting segment was cloned into pGEM T vector (Promega, USA) to prepare pTHSA-TIMP2. The sequence of the HSA-TIMP2 DNA segment was confirmed by sequencing analysis. Then, pTHSA-TIMP2 was cut with XbaI and SpeI. The resulting XbaI/SpeI HSA-TIMP2 gene segment of 1.2 kb was joined to the XbaI-digested pYHSA12(+), a *H. polymorpha* multiple tandem introduction vector having albumin gene inserted (Kang et al., Biotechnol. Bioeng. 76, 175-185, (2001)), to prepare pYHSA13-T2 (FIG. 9).

TABLE 3

PCR primers used in preparation of HSA-TIMP2 fusion gene

| primer | Sequence | Note |
|---|---|---|
| HSA EcoR F | 5' gaattcatgaagtgggtaacctttt 3'<br>(SEQ ID NO: 13) | HSA forward direction |
| Hs-R2 | 5' taagcctaaggcagcttgac 3'<br>(SEQ ID NO: 14) | HSA reverse direction |

TABLE 3-continued

PCR primers used in preparation of HSA-TIMP2 fusion gene

| primer | Sequence | Note |
|---|---|---|
| H-T2-F | 5'caagctgccttaggcttatgcagctgctccccggtg 3'<br>(SEQ ID NO: 15) | Timp2 forward direction, used with 18 bp at HSA C-end in fusion PCR |
| R-T2-Sp | 5' actagtgatttatgggtcctcgatg 3'<br>(SEQ ID NO: 16) | Timp2 reverse direction |

Figure 10:
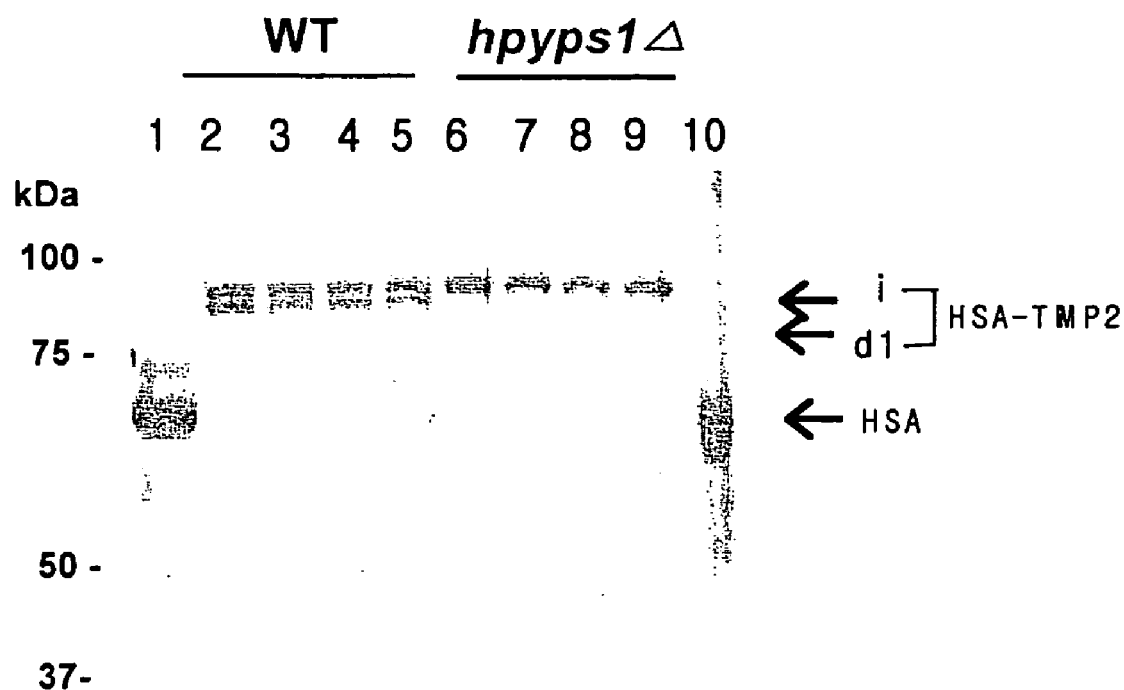
FIG. 10 shows the results of the comparison of the expression and decgradation aspects of recombinant albumin-TIMP2 fusion protein when the *H. polymorpha* wild type strain and the HpYPS1 gene-deleted hpyps1Δ mutant strain are used as a host, in which yeast culture supernatants are analyzed by Western blotting. The Lane 1 represents the wild type transformant transformed with pYHSA12(+), the Lanes 2 to 5 represent the wild type transformant transformed with pYHSA13-TIMP2, the Lanes 6 to 9 represent the hpyps1Δ mutant strain transformed with pYHSA13-TIMP2 and the Lane 10 represent isolated and purified albumin (200 ng).

The albumin fusion protein expression vector prepared above was introduced into *H. polymorpha* DL1-L (leu2) and the hpyps1Δ (leu2 hpyps1::URA3) mutant strain to prepare Leu+ transformants. The collected transformants were passage-cultured five times on selective medium so that the expression vectors could be multiply integrated to the host chromosomal DNA. Then, the transformants were plated at a density of $1 \times 10^5$ to $10^6$ per plate in media containing antibiotic G418 at various concentrations to select transformants having resistance to G418. In order to examine whether the transformants, which had been confirmed to have the expression vector pYHSA13-T2 integrated into the host chromosome by Western blotting, secrets and expresses the fusion protein with an expected size, the yeast culture supernatants obtained by culturing the transformants for 48 hours in YPM was analyzed by Western blotting using antibody to albumin. As shown in FIG. 10, it was observed that the fusion protein HSA-TIMP2 (88 kDa) having an increased size as compared to HSA (66.5 kDa) was secreted as expected. Interestingly, in case of the yapsin deficient mutant strain hpyps1Δ, only 88 kDa HSA-TIMP2 with a whole size was observed without any decomposition product. However, in the wild type DL1 strain, a band being presumed as a decomposition product was observed just under the band of HSA-TIMP2 with a size of 88 kDa. Therefore, due to the reduction of decomposition products, the expressed amount of HSA-Timp2 fusion protein was about two times higher in the hpyps1Δ mutant strain than the wild type strain. This suggests that protein degradation by yapsin1 is inhibited in secretion of recombinant proteins expressed as an albumin-fusion form as well as secretion of the above-described recombinant albumin in the hpyps1Δ mutant strain

INDUSTRIAL APPLICABILITY

The present invention can be usefully used in bioengineering industry to produce a recombinant protein using *H. polymorpha* since cleavage of the recombinant protein by yapsin activity can be remarkably reduced by using *H. polymorpha* strain (hpyps1Δ) with the protease yapsin1 gene being deficient as a recombinant protein-producing host, thereby secreting and producing the recombinant protein in an intact configuration at a high yield.

What is claimed is:

1. An isolated nucleic acid molecule comprising the sequence set forth in SEQ ID NO:1.

2. An isolated nucleic acid molecule which is the HpYPS1 gene encoding *Hansenula polymorpha* yapsin1 deposited under Accession No. KCTC 10285BP.

3. An isolated polypeptide comprising the amino acid sequence set forth in SEQ ID NO:2 which is a yapsin1 protease capable of cleaving a protein comprising a basic amino acid residue or paired, dibasic, amino acid residues.

4. A *Hansenula polymorpha* mutant strain having yapsin1 activity reduced by a mutation or a deletion of the HpYPS1 gene according to claim 1.

5. The *Hansenula polymorpha* mutant strain according to claim 4 deposited under Accession No. KCTC 10281BP.

6. A recombinant *Hansenula polymorpha* strain that is capable of expressing a foreign protein which strain is prepared by transforming the *Hansenula polymorpha* yapsin1 deficient strain according to claim 4 with a gene encoding the foreign protein.

7. A process for preparing and isolating a foreign protein comprising expressing the foreign protein using the *Hansenula polymorpha* yapsin1 deficient strain according to claim 6 as a host, culturing a cell of the strain under conditions suitable for the expression of the foreign protein, and isolating the foreign protein from the cultured *Hansenula polymorpha* yapsin1 deficient strain or the culture medium.

8. The process according to claim 7, in which the foreign protein is a recombinant protein comprising a basic amino acid residue or consecutive dibasic amino acid residues which can be cleaved by the protease having the amino acid sequence set forth in SEQ ID NO:2.

9. The process according to claim 8, in which the protein comprising a basic amino acid residue or paired, dibasic, amino acid residues is selected from the group consisting of human parathyroid hormone, human serum albumin, and an albumin fusion protein.

10. The recombinant *Hansenula polymorpha* strain according to claim 6, which is hpyps1A-pMOXhPTH deposited under Accession No. KCTC 10282BP.

11. A process for preparing and isolating human parathyroid hormone comprising expressing human parathyroid hormone using the *Hansenula polymorpha* yapsin1 deficient strain according to claim 10 as a host.

12. The recombinant *Hansenula polymorpha* strain according to claim 6, which is hpyps1A-pYHSA12 deposited under Accession No. KCTC 10283BP.

13. A process for preparing and isolating human serum albumin comprising expressing human serum albumin using the *Hansenula polymorpha* yapsin1 deficient strain according to claim 12 as a host.

14. The recombinant *Hansenula polymorpha* strain according to claim 6, which is hpyps1A-pYHSA13-TIMP2 deposited under Accession No. KCTC 10485BP.

15. A process for preparing and isolating an albumin fusion protein comprising expressing the albumin fusion protein using the *Hansenula polymorpha* yapsin1 deficient strain according to claim 14 as a host.

* * * * *